United States Patent
Huang et al.

(10) Patent No.: US 10,413,485 B2
(45) Date of Patent: Sep. 17, 2019

(54) COMPOSITION FOR COLORING SKIN AND METHOD FOR COLORING SKIN

(75) Inventors: Lei Huang, Trumbull, CT (US); Qiang Qiu, Trumbull, CT (US); Congling Quan, Trumbull, CT (US); Sheng Meng, Shanghai (CN)

(73) Assignee: CONOPCO, INC., Englewood Cliffs, NJ (US)

( * ) Notice: Subject to any disclaimer, the term of this patent is extended or adjusted under 35 U.S.C. 154(b) by 0 days.

(21) Appl. No.: 14/349,099

(22) PCT Filed: Oct. 8, 2011

(86) PCT No.: PCT/CN2011/001672
§ 371 (c)(1),
(2), (4) Date: Apr. 2, 2014

(87) PCT Pub. No.: WO2013/049956
PCT Pub. Date: Apr. 11, 2013

(65) Prior Publication Data
US 2014/0227332 A1    Aug. 14, 2014

(51) Int. Cl.
| A61K 8/04 | (2006.01) |
| A61K 8/29 | (2006.01) |
| A61K 8/31 | (2006.01) |
| A61Q 1/02 | (2006.01) |
| A61K 8/19 | (2006.01) |
| A61K 8/36 | (2006.01) |
| A61Q 17/04 | (2006.01) |

(52) U.S. Cl.
CPC .................. *A61K 8/04* (2013.01); *A61K 8/19* (2013.01); *A61K 8/29* (2013.01); *A61K 8/31* (2013.01); *A61K 8/361* (2013.01); *A61Q 1/02* (2013.01); *A61K 2800/413* (2013.01); *A61K 2800/43* (2013.01); *A61Q 17/04* (2013.01)

(58) Field of Classification Search
None
See application file for complete search history.

(56) References Cited

U.S. PATENT DOCUMENTS

| 5,308,526 | A | 5/1994 | Dias et al. |
| 5,310,556 | A | 5/1994 | Ziegler |
| 5,312,559 | A | 5/1994 | Kacher |
| 5,496,488 | A | 3/1996 | Kacher et al. |
| 5,658,579 | A | 8/1997 | LaFleur et al. |
| 5,851,978 | A | 12/1998 | Shana'a |
| 5,972,359 | A | 10/1999 | Sine et al. |
| 5,997,890 | A | 12/1999 | Sine et al. |
| 6,174,533 | B1 | 1/2001 | SaNogueira, Jr. et al. |
| 6,432,421 | B1 * | 8/2002 | Brown et al. ................. 424/401 |
| 2005/0100568 | A1 | 5/2005 | De Mul et al. |
| 2007/0167338 | A1 * | 7/2007 | McHugh et al. ............ 510/130 |
| 2008/0152682 | A1 | 6/2008 | Simoulidis et al. |
| 2009/0155321 | A1 | 6/2009 | Harichian et al. |
| 2009/0155322 | A1 | 6/2009 | Harichian et al. |
| 2010/0074928 | A1 * | 3/2010 | Elliott et al. ................. 424/401 |

FOREIGN PATENT DOCUMENTS

| CN | 1088089 | 6/1994 |
| JP | 7508752 | 9/1995 |
| JP | 7508753 | 9/1995 |
| JP | 8511013 | 11/1996 |
| JP | 9512825 | 12/1997 |
| WO | WO9401085 | 1/1994 |
| WO | WO0170188 A1 | 9/2001 |

OTHER PUBLICATIONS

PCT International Search Report PCT/CN2011/001672 dated Dec. 29, 2011.

* cited by examiner

*Primary Examiner* — David J Blanchard
*Assistant Examiner* — Sarah J Chickos
(74) *Attorney, Agent, or Firm* — Foley & Lardner LLP

(57) ABSTRACT

Compositions for coloring skin are described. The compositions comprise beads that comprise petrolatum and optionally a colorant and the beads have a diameter from about 90 to about 625 microns. When applied topically, the compositions unexpectedly yield long lasting color.

15 Claims, No Drawings

COMPOSITION FOR COLORING SKIN AND METHOD FOR COLORING SKIN

FIELD OF THE INVENTION

The present invention is directed to a composition for coloring skin as well as a method for coloring skin. More particularly, the invention is directed to a composition that comprises beads comprising a hydrophobic composition comprising petrolatum and optionally colorant whereby the beads have a diameter from about 90 to about 625 microns. The composition for coloring skin of this invention may be topically applied, has a fatty acid base, and unexpectedly, displays long lasting coloring effects even after three hours of application.

BACKGROUND OF THE INVENTION

Attempts at "perfecting" skin have been made. Often, topical compositions with absorbent fillers (e.g., talc, silica, kaolin) are made wherein such inorganic fillers hide skin imperfections by absorbing some light and simply reflecting light back not unlike paint. An alternative approach is referred to as achieving a soft focus effect. This occurs when incoming light is distorted by scattering (dispersion) wherein light is twisted into a variety of directions. Soft focus is often thought of as a measure similar to haze but applicable to thin product films. Traditional approaches, unfortunately, are not always desired because they tend to not be long lasting. In fact, traditional compositions for providing physical whitening or other color benefits typically do not yield results that last for much more than an hour after application.

There is an increasing interest to develop compositions for coloring skin wherein the coloring effects are long lasting. This invention, therefore, is directed to a composition for coloring skin as well as a method for skin coloring. The composition comprises beads comprising a hydrophobic composition comprising petrolatum and optionally colorant whereby the beads have a diameter from about 90 to about 625 microns. The composition of this invention may be topically applied, has a fatty acid base, and unexpectedly, displays long lasting coloring effects even after three hours of application.

Additional Information

Efforts have been disclosed for making compositions that impart a soft focus. In U.S. Patent application No. 2008/0152682, single-crystal platy barium sulfate containing compositions are described.

Still other efforts have been disclosed for making topical compositions that improve skin characteristics. In U.S. Patent Application Nos. 2005/0100568 and 2009/0155321, cosmetic compositions for improving skin appearance are described.

Even other efforts have been disclosed for making topical compositions that improve skin characteristics. In U.S. Pat. Nos. 5,658,579, 5,972,359, 5,997,890 and 6,174,533, topical compositions for covering skin imperfections are described.

Further, additional efforts for making topical compositions are described in World Application WO 01/70188, the same describing low pH and high fatty acid vanishing creams.

None of the additional information above describes a composition suitable for long lasting coloring of skin, the composition comprising a fatty acid base and beads comprising a hydrophobic composition comprising petrolatum and optionally colorant whereby the beads have a diameter from about 90 to about 625 microns.

SUMMARY OF THE INVENTION

In a first aspect, the present invention is directed to a composition for topical application, the composition comprising:
(a) a bead comprising
  (i) a hydrophobic composition comprising petrolatum; and
  (ii) optionally colorant;
(b) a cosmetically acceptable carrier comprising at least 8% by weight of $C_{16}$ to $C_{20}$ fatty acid, the fatty acid being at least 32% by weight $C_{18}$ fatty acid and including any salts thereof
wherein the bead has a diameter from about 90 to about 625 microns and further wherein the weight ratio of hydrophobic composition comprising petrolatum and colorant/fatty acid (i.e., h+c/a ratio) is at least 0.02.

In a second aspect, the present invention is directed to a method for coloring skin comprising the step of contacting skin with the composition of the first aspect of this invention.

In a third aspect, the present invention is directed to a method for making the composition of the first aspect of this invention.

All other aspects of the present invention will more readily become apparent upon considering the detailed description and examples which follow.

Skin, as used herein, is meant to include skin on the face, neck, chest, back, arms (including underarms), hands, legs, buttocks and scalp. Bead, as used herein, is meant to mean a bead (or particle) that has a diameter from about 90 to about 625 microns where diameter is meant to mean the longest measurable (cross-sectional) distance in the event the bead is not a perfect sphere. Colorant is meant to be embedded within a composition comprising petrolatum to form the preferred bead, and preferably, homogeneously mixed therein. Long-lasting, as used herein, generally means a composition capable of physically delivering color to skin for an extended period. For example, as it relates to whitening, long lasting is meant to mean whitening defined as a delta L*% value (CIELAB color scale) change of 45 to 70% higher for at least 200 minutes after application as compared when no composition consistent with this invention is used and a composition having whitening capabilities is used but not with a bead comprising petrolatum as described herein and as determined by using a Hunter Lab Labscan XE instrument. L*% is the percent difference of the whiteness reading Immediately after application against a whiteness reading at a selected time interval. Composition for coloring skin, as used herein, is meant to mean a composition that affects skin complexion wherein the same can be and preferably is a leave-on composition, and most preferably, a vanishing cream or lotion. The weight ratio h+c/a means the weight amount of hydrophobic composition comprising petrolatum plus the weight amount of optional colorant divided by the weight amount of fatty acid in the composition for coloring skin. For the avoidance of doubt, c, weight amount of optional colorant, can have a value of zero. Particle, as used herein, is meant to mean a single particle as well as an agglomerate or large particle made of smaller particles. The $C_{15}$ to $C_{20}$ fatty acid as described herein is meant to include any cosmetically acceptable salts thereof such as, for example, sodium, potassium and amine derived salts thereof.

Comprising, as used herein, is meant to include consisting essentially of and consisting of. For the avoidance of doubt, therefore, the bead of this invention may consist essentially of or consist of petrolatum and optionally colorant with the often preferred colorant being iron oxide and especially iron oxide red. All ranges identified herein are meant to include all ranges subsumed therein if, for example, reference to the same is not explicitly made.

DETAILED DESCRIPTION OF THE PREFERRED EMBODIMENTS

The only limitation with respect to the bead comprising hydrophobic composition comprising petrolatum and optional colorant used in this invention is that the same comprises a diameter from about 90 to about 625 microns, and preferably, from about 150 to about 450 microns, and most preferably, from about 175 to about 325 microns, including all ranges subsumed therein.

In an often preferred embodiment, the weight of hydrophobic composition comprising petrolatum in the bead is from about 30 to about 95 times, and most preferably, from about 35 to about 90 times, and optimally, from about 38 to about 80 times more than the weight of colorant (i.e., when used) in the bead, based on total weight of the bead and including all ranges subsumed therein. The total weight of hydrophobic composition comprising petrolatum is often from about 1 to about 4.0%, and preferably, from about 1.5 to about 3.5%, and most preferably, from about 1.5 to about 3.0% by weight based on total weight of the composition for coloring skin and including all ranges subsumed herein. The total weight of colorant, when used, is often from about 0.02 to about 0.15%, and preferably, from about 0.02 to about 0.11%, and most preferably, from about 0.01 to about 0.06% by weight based on total weight of the composition for coloring skin and including all ranges subsumed therein.

The hydrophobic composition comprising petrolatum may further comprise additional hydrophobic materials like, for example, mineral oil, isoparaffins, polyalphaolefins, isohexadecane, siliconized waxes like siliconized beeswax, shea butter, candelilla, carnauba, silicones, glycerides (like sunflower seed oil, soybean oil, safflower oil), mixtures thereof or the like. The combination of materials used for the hydrophobic composition comprising petrolatum is limited only to the extent that the materials may be topically applied and the hydrophobic composition has a melting point from about 40° to about 50° C., and preferably, from about 42° to about 48° C., including all ranges subsumed therein. In another often desired embodiment, the hydrophobic composition comprises at least 50% by weight petrolatum, and preferably, from 75 to 100% by weight petrolatum, and most preferably, 100% by weight petrolatum based on total weight of the hydrophobic composition comprising petrolatum.

When making the bead of the present invention, hydrophobic composition comprising petrolatum is heated from about 40° to about 65° C., and preferably, from about 42° to about 60° C., and most preferably, from about 48° to 55° C., including all ranges subsumed therein. In an optional but preferred embodiment, colorant is combined with hydrophobic composition comprising petrolatum and mixed. Mixing and heating is controlled wherein heating should be at the same temperature described as if only hydrophobic composition comprising petrolatum is used. Mixing and heating should continue until a preferably homogeneous composition of colorant and hydrophobic composition comprising petrolatum is produced.

The heated composition comprising hydrophobic composition comprising petrolatum (and optionally but preferably colorant) should then be added to or combined with cosmetically acceptable carrier comprising at least about 8% by weight $C_{16}$ to $C_{20}$ fatty acid. Preferably, the carrier comprises from about 8 to about 50%, and most preferably, from about 10 to about 25%, and optimally, from about 12 to 20% by weight $C_{16}$ to $C_{20}$ fatty acid based on total weight of the composition for coloring skin and including all ranges subsumed therein. Carrier is typically maintained at a temperature from about 25° to about 48° C., and preferably, from about 30° to about 45° C., and most preferably, from about 30° to about 40° C., including all ranges subsumed therein. Composition comprising petrolatum (and optionally colorant) should be maintained at a temperature that is higher than the temperature of the cosmetically acceptable carrier prior to combining. Stirring should be maintained at a rate and for a time that results in composition comprising petrolatum (and optionally colorant) becoming beads of diameter described herein within the carrier. Often at least 32% by weight of the fatty acid used is $C_{18}$ fatty acid. Preferably, from about 35 to 100% by weight of the fatty acid used herein is $C_{18}$ fatty acid. Most preferably, from 40 to 60% by weight of all fatty acid used is $C_{18}$ fatty acid. In a most especially preferred embodiment the fatty acid used herein is a mixture of $C_{16}:C_{18}$ fatty acid at a weight ratio of about 60:40 to about 40:60, including all ratios subsumed therein.

In an especially preferred embodiment, the h+c/a ratio is from about 0.02 to about 0.5, and most preferably, from about 0.03 to about 0.3, including all ranges subsumed therein. Optimally, the h+c/a ratio is from about 0.1 to about 0.18

The only limitation with respect to the type of colorant that may optionally be used in this invention is that the colorant is one that can be mixed with hydrophobic composition comprising petrolatum, and preferably, homogenously mixed with the hydrophobic composition. Illustrative yet non-limiting examples of the type of colorant suitable for use in this invention are titanium dioxide, zinc oxide, iron oxide, cromium oxide, dye, organic lake, carotenoid like lycopene, mixtures thereof or the like. Typically the colorant used is a particle having a diameter from about 100 to about 1200 nm, and preferably, from about 280 to about 1000 nm, and most preferably, from about 300 to about 650 nm, including all ranges subsumed therein. Consistent with the diameter for the beads, diameter for the colorant is meant to mean the longest measurable distance of a cross-section of the particle in the event the particle is not a perfect sphere.

Compositions of the present invention will typically include cosmetically acceptable carrier components in addition to the fatty acid described herein. Water is the most preferred additional carrier. Amounts of water may range from about 1 to about 99%, and preferably, from about 5 to about 90%, and most preferably, from about 35 to about 80%, and optimally, from about 40 to about 75% by weight, based on total weight of the composition for coloring skin and including all ranges subsumed therein. Ordinarily the compositions of this invention will be water and oil emulsions, most preferably, of the oil-in-water variety. Water-in-oil emulsions, and especially, those generally classified as water-in-oil and high internal phase emulsions are, however, an option. Illustrative examples of the high internal phase emulsions suitable to carry the beads of this invention are described in commonly owned U.S. Patent Application Publication Nos. 2008/0311058 and 2009/0247445, the disclosures of which are incorporated herein by reference.

Other cosmetically acceptable carriers suitable for use in this invention may include mineral oils, silicone oils, synthetic or natural esters, and alcohols. Amounts of these materials may range from about 0.1 to about 50%, and preferably, from about 0.1 to about 30%, and most preferably, from about 1 to about 20% by weight of the composition, including all ranges subsumed therein.

Silicone oils may be divided into the volatile and nonvolatile variety. The term "volatile" as used herein refers to those materials which have a measurable vapor pressure at ambient temperature. Volatile silicone oils are preferably chosen from cyclic or linear polydimethylsiloxanes containing from about 3 to about 9, and preferably, from about 4 to about 5 silicon atoms.

Linear volatile silicone materials generally have viscosities of less than about 5 centistokes at 25° C. while cyclic materials typically have viscosities of less than about 10 centistokes.

Nonvolatile silicone oils useful as carrier material include polyalkyl siloxanes, polyalkylaryl siloxanes and polyether siloxane copolymers. The essentially non-volatile polyalkyl siloxanes useful herein include, for example, polydimethylsiloxanes (like dimethicone) with viscosities of from about 5 to about 100,000 centistokes at 25° C.

An often preferred silicone source is a cyclopentasiloxane and dimethiconol solution.

Among suitable esters are:
(1) Alkenyl or alkyl esters of fatty acids having 10 to 20 carbon atoms like isopropyl palmitate, isopropyl isostearate, isononyl isonanonoate, oleyl myristate, isopropyl myristate, oleyl stearate, and oleyl oleate;
(2) Ether-esters such as fatty acid esters of ethoxylated fatty alcohols;
(3) Polyhydric alcohol esters such as ethylene glycol mono- and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters;
(4) Wax esters such as beeswax, spermaceti, myristyl myristate, stearyl stearate; and
(5) Sterol esters, of which soya sterol and cholesterol fatty acid esters are examples thereof.

Emulsifiers may be present in the composition for coloring skin of the present invention. Total concentration of the emulsifier may range from about 0.1 to about 40%, and preferably, from about 1 to about 20%, and most preferably, from about 1 to about 5% by weight of the composition, including all ranges subsumed therein. The emulsifier may be selected from the group consisting of anionic, nonionic, cationic and amphoteric actives. Particularly preferred nonionic actives are those with a $C_{10}$-$C_{20}$ fatty alcohol or acid hydrophobe condensed with from about 2 to about 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; and polyoxyethylene sorbitan as well as combinations thereof. Alkyl polyglycosides and saccharide fatty amides (e.g. methyl gluconamides) are also suitable nonionic emulsifiers.

Preferred anionic emulsifiers include alkyl ether sulfate and sulfonates, alkyl sulfates and sulfonates, alkylbenzene sulfonates, alkyl and dialkyl sulfosuccinates, $C_8$-$C_{20}$ acyl isethionates, $C_8$-$C_{20}$ alkyl ether phosphates, alkylethercarboxylates and combinations thereof.

Cationic emulsifiers that may be used include, for example, palmitamidopropyltrimonium chloride, distearyldimonium chloride and mixtures thereof. Useful amphoteric emulsifiers include cocoamidopropyl betaine, $C_{12}$-$C_{20}$ trialkyl betaines, sodium lauroamphoacetate, and sodium laurodiamphoacetate or a mixture thereof.

Other generally preferred emulsifiers include glyceryl stearate, glycol stearate, stearamide AMP, PEG-100 stearate, cetyl alcohol as well as emulsifying/thickening additives like hydroxyethylacrylate/sodium acryloyldimethyl taurates copolymer/squalane and mixtures thereof.

Preservatives can desirably be incorporated into the compositions for coloring skin of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are Iodopropynyl butyl carbamate, phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from about 0.01% to about 2% by weight of the composition, including all ranges subsumed therein.

Thickening agents may optionally be included in compositions of the present invention. Particularly useful are the polysaccharides. Examples include starches, natural/synthetic gums and cellulosics. Representative of the starches are chemically modified starches such as sodium hydroxypropyl starch phosphate and aluminum starch octenylsuccinate. Tapioca starch is often preferred. Suitable gums include xanthan, sclerotium, pectin, karaya, arabic, agar, guar, carrageenan, alginate and combinations thereof. Suitable cellulosics include hydroxypropyl cellulose, hydroxypropyl methylcellulose, ethylcellulose and sodium carboxy methylcellulose. Synthetic polymers are yet another class of effective thickening agent. This category includes cross-linked polyacrylates such as the Carbomers, polyacrylamides such as Sepigel® 305 and taurate copolymers such as Simulgel EG® and Aristoflex® AVC, the copolymers being identified by respective INCI nomenclature as Sodium Acrylate/Sodium Acryloyldimethyl Taurate and Acryloyl Dimethyltaurate/Vinyl Pyrrolidone Copolymer. Another preferred synthetic polymer suitable for thickening is an acrylate-based polymer made commercially available by Seppic and sold under the name Simulgel INS100.

Amounts of the thickener, when used, may range from about 0.001 to about 5%, and preferably, from about 0.1 to about 2%, and most preferably, from about 0.2 to about 0.5% by weight of the composition including all ranges subsumed therein.

Fragrances, fixatives and abrasives may optionally be included in compositions of the present invention. Each of these substances may range from about 0.05 to about 5%, preferably between 0.1 and 3% by weight.

To enhance skin moisturization, cationic ammonium compounds may optionally be used in the compositions of this invention. Such compounds include salts of hydroxypropyltri ($C_1$-$C_3$ alkyl) ammonium mono-substituted-saccharide, salts of hydroxypropyltri ($C_1$-$C_3$ alkyl) ammonium mono-substituted polyols, dihydroxypropyltri ($C_1$-$C_3$ alkyl) ammonium salts, dihydroxypropyldi ($C_1$-$C_3$ alkyl) mono (hydroxyethyl) ammonium salts, guar hydroxypropyl trimonium salts, 2,3-dihydroxypropyl tri($C_1$-$C_3$ alkyl or hydroxalkyl) ammonium salts or mixtures thereof. In a most preferred embodiment and when desired, the cationic ammonium compound employed in this invention is the quaternary ammonium compound 1,2-dihydroxypropyltrimonium chloride. If used, such compounds typically make up from about 0.01 to about 30%, and preferably, from about 0.1 to about 15% by weight of the composition.

When cationic ammonium compounds are used, preferred additives for use with the same are moisturizing agents such as substituted ureas like hydroxymethyl urea, hydroxyethyl urea, hydroxypropyl urea; bis(hydroxymethyl)urea; bis(hydroxyethyl)urea; bis(hydroxypropyl)urea; N,N'-dihydroxymethyl urea; N,N'-di-hydroxyethyl urea; N,N'-di-hydroxypropyl urea; N,N,N'-tri-hydroxyethyl urea; tetra(hydroxymethyl)urea; tetra(hydroxyethyl)urea; tetra(hydroxypropyl)urea; N-methyl-N'-hydroxyethyl urea; N-ethyl-N,N—N'-hydroxyethyl urea; N-hydroxypropyl-N'-hydroxyethyl urea and N,N'-dimethyl-N-hydroxyethyl urea or mixtures thereof. Where the term hydroxypropyl appears, the meaning is generic for either 3-hydroxy-n-propyl, 2-hydroxy-n-propyl, 3-hydroxy-i-propyl or 2-hydroxy-i-propyl radicals. Most preferred is hydroxyethyl urea. The latter is available as a 50% aqueous liquid from the National Starch & Chemical Division of ICI under the trademark Hydrovance.

Amounts of substituted urea, when used, in the composition of this invention range from about 0.01 to about 20%, and preferably, from about 0.5 to about 15%, and most preferably, from about 2 to about 10% based on total weight of the composition and including all ranges subsumed therein.

Conventional humectants may be employed in the present Invention. These are generally polyhydric alcohol-type materials. Typical polyhydric alcohols include glycerol (i.e., glycerine or glycerin), propylene glycol, dipropylene glycol, polypropylene glycol, polyethylene glycol, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. Most preferred is glycerin, propylene glycol or a mixture thereof. The amount of humectant employed may range anywhere from 0.5 to 20%, preferably between 1 and 15% by weight of the composition.

When cationic ammonium compound and substituted urea are used, in a most especially preferred embodiment at least from about 1 to about 15% glycerin external to the bead is used, based on total weight of the composition and including all ranges subsumed therein.

Compositions of the present invention may include vitamins. Illustrative vitamins are Vitamin A (retinol) as well as retinol esters like retinol palmitate and retinol propionate, Vitamin $B_2$, Vitamin $B_3$ (niacinamide), Vitamin $B_6$, Vitamin C, Vitamin E, Folic Acid and Biotin. Derivatives of the vitamins may also be employed. For instance, Vitamin C derivatives include ascorbyl tetraisopalmitate, magnesium ascorbyl phosphate and ascorbyl glycoside. Derivatives of Vitamin E include tocopheryl acetate, tocopheryl palmitate and tocopheryl linoleate. DL-panthenol and derivatives may also be employed. Total amount of vitamins when present in compositions according to the present invention may range from 0.001 to 10%, preferably from 0.01% to 1%, optimally from 0.1 to 0.5% by weight of the composition.

Other optional additives suitable for use in this invention include resorcinols like 4-ethyl resorcinol, 4-hexyl resorcinol, 4-phenylethyl resorcinol, dimethoxytoluyl propyl resorcinol, 4-cyclopentyl resorcinol, 4-cyclohexylresorcinol, alpha- and/or beta-hydroxyacids, petroselinic acid, conjugated linoleic acid, mixtures thereof or the like. Such additives, when used, collectively make up from about 0.001 to about 12% by weight of the composition.

Desquamation promoters may be present. Illustrative are the alpha-hydroxycarboxylic acids, beta-hydroxycarboxylic acids. The term "acid" is meant to include not only the free acid but also salts and $C_1$-$C_{30}$ alkyl or aryl esters thereof and lactones generated from removal of water to form cyclic or linear lactone structures. Representative acids are glycolic and its derivatives, lactic and malic acids. Salicylic acid is representative of the beta-hydroxycarboxylic acids. Amounts of these materials when present may range from about 0.01 to about 15% by weight of the composition.

A variety of herbal extracts may optionally be included in compositions of this Invention. The extracts may either be water soluble or water-insoluble carried in a solvent which respectively is hydrophilic or hydrophobic. Water and ethanol are the preferred extract solvents. Illustrative extracts include those from green tea, yarrow, chamomile, licorice, aloe vera, grape seed, citrus unshui, willow bark, sage, thyme and rosemary.

Also optionally suitable for use include materials like chelators (e.g., EDTA), opacifiers (like $TiO_2$, particle size from 50 to 1200 nm, and preferably, 50 to 350 nm), $C_{8-22}$ fatty acid substituted saccharides, lipoic acid, retinoxytrimethylsilane (available from Clariant Corp. under the Silcare 1M-75 trademark), dehydroepiandrosterone (DHEA) and combinations thereof. Ceramides (including Ceramide 1, Ceramide 3, Ceramide 36 and Ceramide 6) as well as pseudoceramides may also be useful. Amounts of these materials may range from about 0.000001 to about 10%, preferably from about 0.0001 to about 1% by weight of the composition.

Sunscreen actives may also be included in compositions of the present invention. Particularly preferred are such materials as ethylhexyl p-methoxycinnamate, available as Parsol MCX®, Avobenzene, available as Parsol 1789® and benzophenone-3, also known as Oxybenzone. Inorganic sunscreen actives may be employed such as microfine titanium dioxide, zinc oxide, polyethylene and various other polymers. Amounts of the sunscreen agents when present may generally range form 0.1 to 30%, preferably from 0.5 to 20%, optimally from 0.75 to 10% by weight.

Conventional buffers/pH modifiers may be used. These include commonly employed additives like sodium hydroxide, potassium hydroxide, hydrochloric acid, citric acid and citrate/citric acid buffers. In an especially preferred embodiment, the pH of the composition of this invention is from about 4 to about 8, and preferably, from about 4.25 to about 7.75, and most preferably, from about 6 to about 7.5, including all ranges subsumed therein.

A wide variety of packaging can be employed to store and deliver the composition for coloring skin of this invention. Packaging is often dependent upon the type of personal care end-use. For instance, leave-on skin lotions and creams, shampoos, conditioners and shower gels generally employ plastic containers with an opening at a dispensing end covered by a closure. Typical closures are screw-caps, non-aerosol pumps and flip-top hinged lids. Packaging for antiperspirants, deodorants and depilatories may involve a container with a roll-on ball on a dispensing end. Alternatively these types of personal care products may be delivered in a stick composition formulation in a container with propel-repel mechanism where the stick moves on a platform towards a dispensing orifice. Metallic cans pressurized by a propellant and having a spray nozzle serve as packaging for antiperspirants, shave creams and other personal care products. Toilette bars may have packaging constituted by a cellulosic or plastic wrapper or within a cardboard box or even encompassed by a shrink wrap plastic film.

The following examples are provided to facilitate an understanding of the present invention. The examples are not intended to limit the scope of the claims.

Example 1

A base composition was made by combining the ingredients described below and mixing with moderate shear. Heat was provided and ranged from about 50° to about 80° C. The desired base composition was obtained in about 45 minutes.

TABLE 1

| Ingredient | % by weight |
|---|---|
| Fatty acid (55% $C_{16}$ and 45% $C_{18}$) | 18.0 |
| Emulsifier | 0.5 |
| TiO2 | 0.80 |
| Dimethicone (DC200, 350 Cst) | 0.80 |
| Parsol MCX | 1.3 |
| Parsol 1789 | 0.40 |
| Preservative | 0.5 |
| Glycerin | 1.00 |
| Chelator | 0.04 |
| Buffer | pH 7 |
| Water | Balance |

The resulting varnishing cream base composition was cooled and maintained at a temperature of about 32° C. Homogeneous composition comprising petrolatum and $Fe_2O_3$ (2.5% and 0.05%, respectively based on total weight of the final composition for coloring skin) was prepared by mixing the same and heating to a temperature of about 48° C. The homogeneous composition obtained was combined with the base composition. Stirring continued for a period of time to yield composition for coloring skin having beads of about 225 microns homogeneously dispersed in the composition for coloring skin where the final composition had about 2.5% petrolatum and 0.05% $Fe_2O_3$.

Example 2

The composition for coloring skin of this invention made in Example 1 was assessed for long lasting whitening. The composition was applied to a color assessing canvas laminate plates (made available from MSC Industrial Supply Company), the plates being treated with the composition of this invention (75 micron film applied with a conventional film applicator). The coated plate was assessed for color longevity (i.e., whiteness) for about 200 minutes. The procedure was repeated for the control which was a commercially available varnishing cream with about 0.8 TiO2 in the base and 18% stearic acid. The control had no beads consistent with this invention. Color longevity for the samples (as reported in Table 2) was monitored using a HunterLab Labscan XE Colorimeter.

TABLE 2

| Composition of Example 2 | | Control | |
|---|---|---|---|
| delta L* % | Time | delta L* % | Time |
| 100 | 1 second | 100 | 1 second |
| 100 | 5 minutes | 95 | 5 minutes |
| 100 | 10 minutes | 87 | 10 minutes |
| 99 | 25 minutes | 30 | 25 minutes |
| 98 | 50 minutes | 30 | 50 minutes |
| 96 | 60 minutes | 30 | 60 minutes |
| 95 | 70 minutes | 33 | 70 minutes |
| 90 | 80 minutes | 32 | 80 minutes |
| 80 | 90 minutes | 32 | 80 minutes |
| 72 | 100 minutes | 32 | 80 minutes |
| 63 | 110 minutes | 32 | 80 minutes |
| 62 | 120 minutes | 32 | 80 minutes |
| 61 | 130 minutes | 32 | 80 minutes |
| 60 | 140 minutes | 32 | 80 minutes |
| 60 | 150 minutes | 32 | 80 minutes |
| 60 | 180 minutes | 32 | 180 minutes |
| 60 | 200 minutes | 32 | 200 minutes |

The results surprisingly show that compositions made according to the invention maintain significantly better color longevity when compared to a control composition.

Example 3

The composition of this Example was made in a manner similar to the one described in Example 1 except that no $Fe_2O_3$ was used with the petrolatum. The composition of this Example, which contained 2.5% by weight petrolatum, was assessed in a manner similar to the one described in Example 2. Color longevity for the samples (as reported in Table 3) was monitored as described in Example 2.

TABLE 3

| Composition of Example 3 | |
|---|---|
| delta L* % | Time |
| 100 | 1 second |
| 99 | 1 minute |
| 99 | 3 minutes |
| 99 | 5 minutes |
| 99 | 10 minutes |
| 99 | 15 minutes |
| 99 | 20 minutes |
| 98 | 25 minutes |
| 98 | 30 minutes |
| 97 | 35 minutes |
| 97 | 40 minutes |
| 96 | 45 minutes |
| 96 | 50 minutes |
| 95 | 55 minutes |
| 94 | 60 minutes |
| 93 | 65 minutes |
| 91 | 70 minutes |
| 89 | 75 minutes |
| 86 | 80 minutes |
| 83 | 85 minutes |
| 82 | 90 minutes |
| 80 | 95 minutes |
| 76 | 100 minutes |
| 74 | 105 minutes |
| 71 | 110 minutes |
| 69 | 115 minutes |
| 68 | 120 minutes |

TABLE 3-continued

Composition of Example 3

| delta L* % | Time |
|---|---|
| 67 | 125 minutes |
| 67 | 140 minutes |
| 67 | 170 minutes |
| 67 | 190 minutes |

The results surprisingly show that compositions made according to this invention maintain significantly better color longevity when compared to the control composition of Example 2.

What is claimed:

1. A composition for topical application, the composition comprising:
    (a) a bead consisting of
        (i) a hydrophobic composition, wherein 75 to 100% by weight of the hydrophobic composition is petrolatum; and
        ii) colorant, wherein the colorant is selected from the group consisting of titanium dioxide, zinc oxide, iron oxide, organic lake, dye, chromium oxide, lycopene or mixtures thereof;
    (b) a cosmetically acceptable carrier comprising at least 0.8% by weight of $C_{16}$ to $C_{20}$ fatty acid and salts thereof;
    wherein:
    the bead has a diameter from 90 to 625 microns, an h+c/a ratio that is from 0.02 to 0.5; the $C_{16}$ to $C_{20}$ fatty acid has a mixture of $C_{16}$:$C_{20}$ fatty acid at weight ratio of about 60:40 to about 40:60;
    the composition for topical application is a water-in-oil emulsion comprising from about 1 to about 99% by weight water; and
    the colorant makes up from 0.01 to 0.15% by weight of the total weight of the composition for topical application.

2. The composition according to claim 1 wherein the bead has a diameter from 175 to 325 microns.

3. The composition according to claim 1 wherein the hydrophobic composition consists of petrolatum and one or more of sorbitol, glycerin, siliconized beeswax, siliconized shea butter, siliconized candelilla, siliconized carnauba, sunflower oil, safflower oil, or soybean oil.

4. The composition according to claim 1 wherein the bead has a melting point from 40° to 50° C.

5. The composition according to claim 1 wherein the colorant is selected from the group consisting of titanium dioxide, iron oxide, and zinc oxide.

6. The composition according to claim 2 wherein the h+c/a ratio is from 0.03 to 0.3.

7. The composition according to claim 1 wherein the colorant is iron oxide red.

8. The composition according to claim 1 wherein the colorant is a particle or agglomerate having a diameter from 100 to 1200 nm.

9. The composition according to claim 1 wherein the colorant is present and makes up from 0.01 to 0.06% of the composition.

10. The composition according to claim 1 wherein the hydrophobic composition makes up from 1 to 4% by weight of the composition.

11. The composition according to claim 1 wherein the composition further comprises sunscreen, niacinamide, 4-ethyl resorcinol, 4-hexyl resorcinol 4-phenylethyl recorsinol, petroselinic acid conjugated linoleic acid, tocophenyl acetate, tocopheryl palmitate, tocopheryl linoleate or retinol palmitate.

12. The composition according to claim 1 wherein the composition is a vanishing cream and water makes up from about 35% to about 80% by weight of the composition.

13. A method for coloring skin, the method comprising the step of contacting skin with the composition for topical application of claim 1.

14. The composition according to claim 1 wherein the bead has a diameter from about 150 to about 450 microns, the composition comprising niacinamide and having a pH from about 4 to about 8, and further wherein the hydrophobic composition comprising petrolatum makes up from about 1 to about 3.5% by weight of the composition for coloring skin.

15. The composition according to claim 1 wherein the bead has a diameter from about 175 to about 325 microns and the composition comprises a resorcinol, sunscreen or retinol palmitate, and phenoxyethanol.

* * * * *